(12) United States Patent
Haarstad et al.

(10) Patent No.: US 6,533,753 B1
(45) Date of Patent: Mar. 18, 2003

(54) APPARATUS AND METHOD FOR THE TREATMENT OF AN OCCLUDED LUMEN

(76) Inventors: Philip Haarstad, 1054 Elsbree La., Windsor, CA (US) 95492; Beau Fisher, 6401 Montecito Blvd. Apt. 2, Santa Rosa, CA (US) 95409; Kevin Drisko, 529 Christopher Way, Windsor, CA (US) 95492

(*) Notice: Subject to any disclaimer, the term of this patent is extended or adjusted under 35 U.S.C. 154(b) by 0 days.

(21) Appl. No.: 09/544,750

(22) Filed: Apr. 7, 2000

(51) Int. Cl.[7] .................................................. A61M 29/00
(52) U.S. Cl. ................................................... 604/96.01
(58) Field of Search ........................ 604/500, 507–510, 604/164.13, 96.01, 103.07, 100.03, 101.01, 101.05

(56) References Cited

U.S. PATENT DOCUMENTS

| | | |
|---|---|---|
| 3,833,004 A | 9/1974 | Vazquez et al. |
| 4,863,424 A | 9/1989 | Blake, III et al. |
| 4,961,738 A | 10/1990 | Mackin |
| 5,304,199 A * | 4/1994 | Myers ......................... 606/194 |

FOREIGN PATENT DOCUMENTS

| | | |
|---|---|---|
| EP | 0 351 734 | 1/1990 |
| EP | 0 359 489 | 3/1990 |

* cited by examiner

Primary Examiner—Edward K. Look
Assistant Examiner—Dwayne J. White

(57) ABSTRACT

An apparatus for improved centering of a device which is intended to penetrate a severe occlusion of a body lumen. The apparatus includes a substantially tubular member having an exit port; an inflatable member having a distal end; wherein the exit port is not distal to the inflatable member. Such an apparatus allows for better fluoroscopic visualization, and therefore placement, of the apparatus with respect to the lesion.

8 Claims, 9 Drawing Sheets

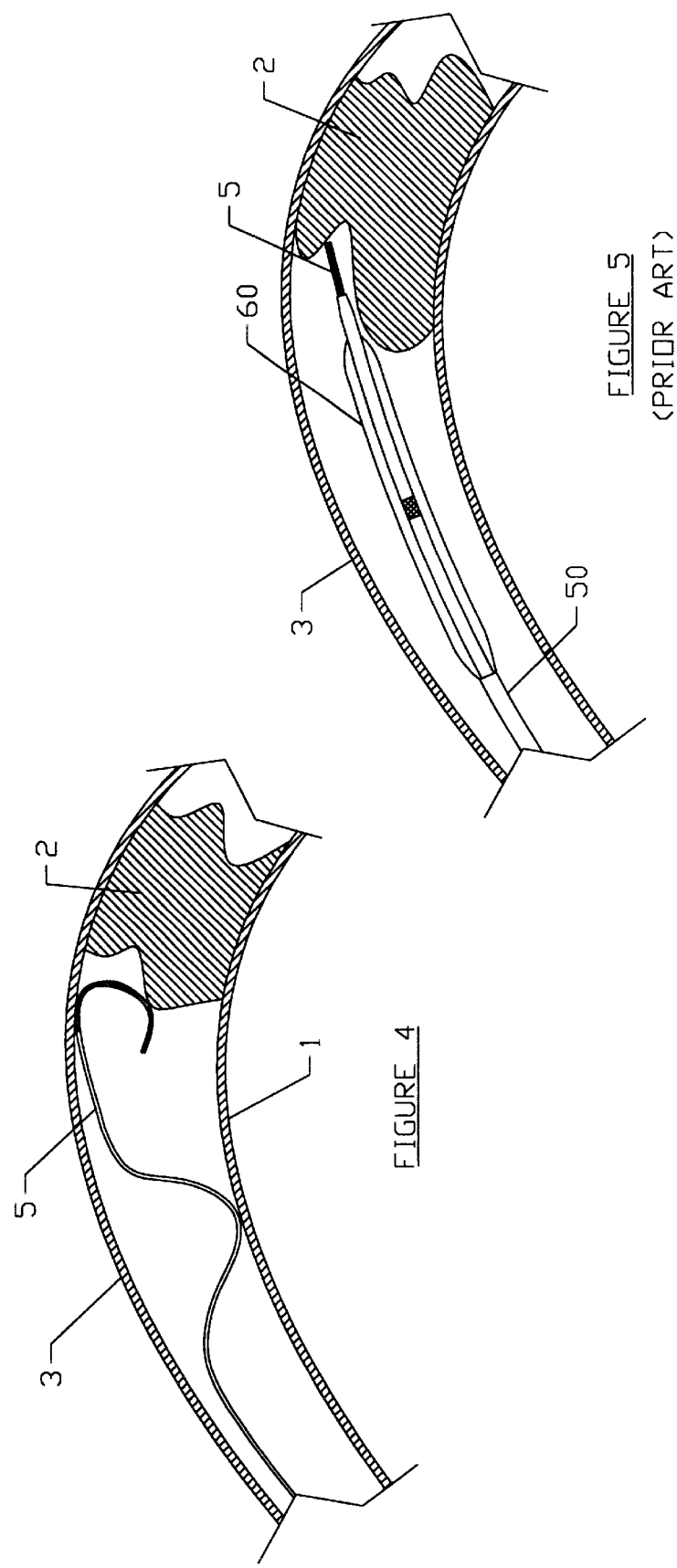

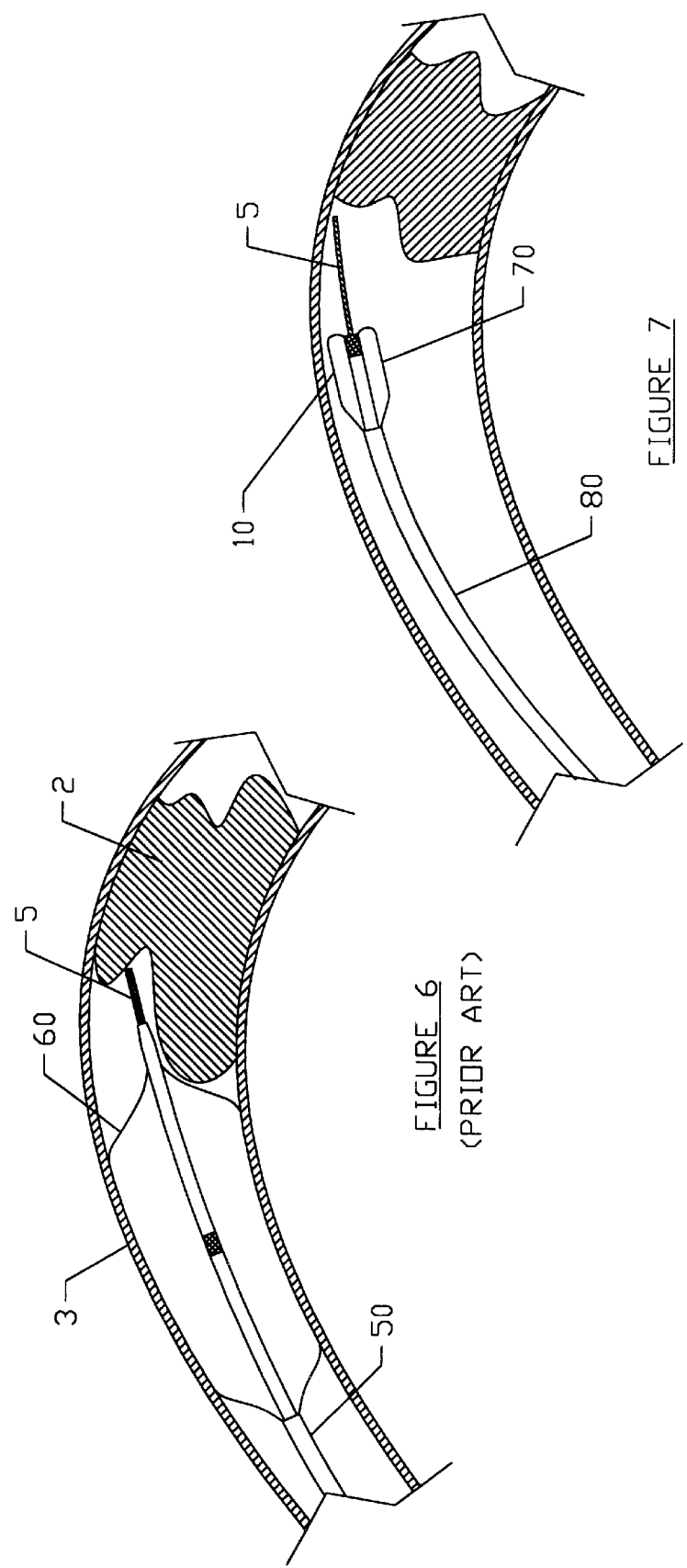

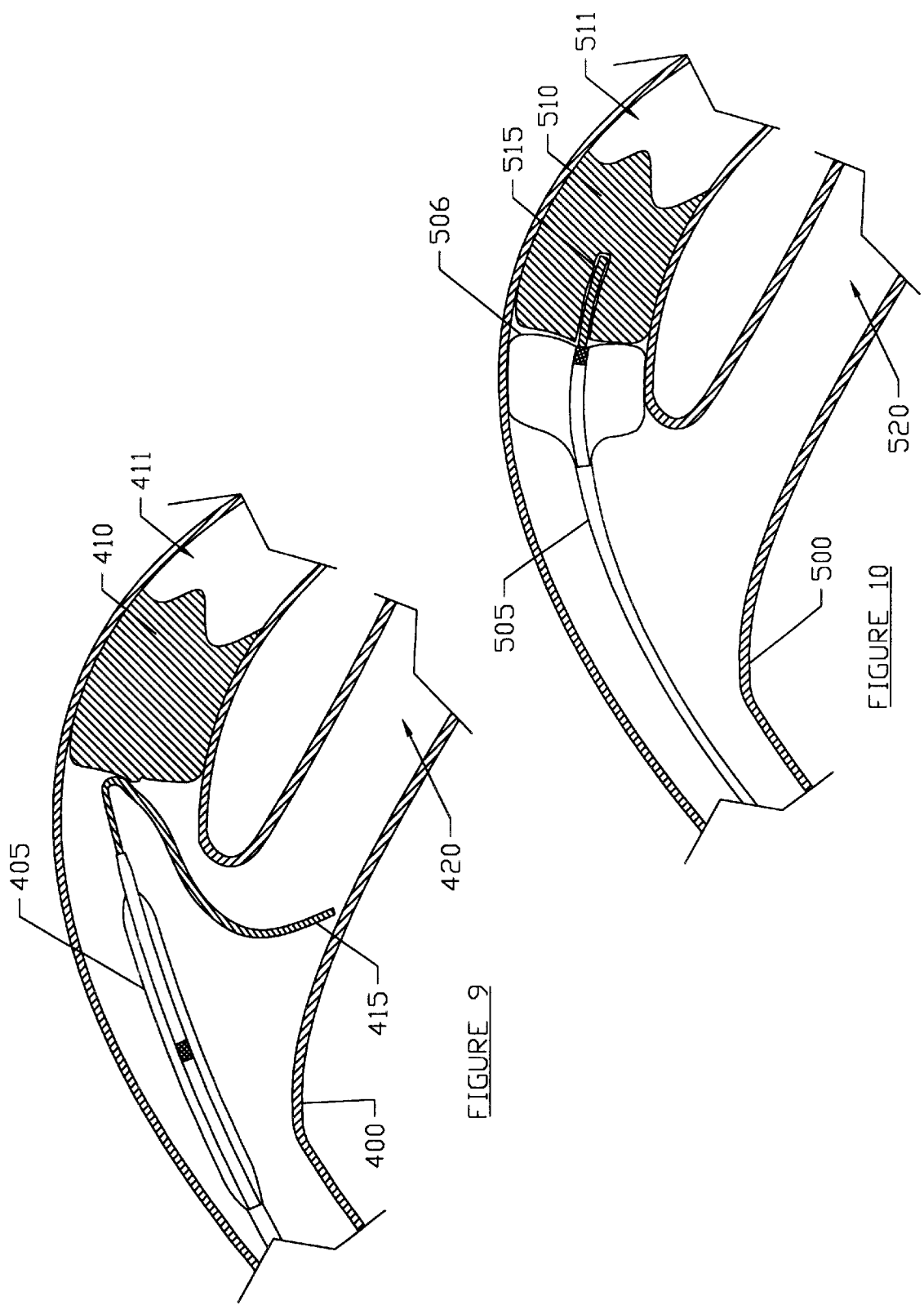

APPARATUS AND METHOD FOR THE TREATMENT OF AN OCCLUDED LUMEN

FIELD OF THE INVENTION

The present invention relates generally to an apparatus and method for treatment of stenotic or diseased lumens. More particularly, the invention relates to a novel balloon catheter and method of treatment of a chronic total occlusion of a lumen.

BACKGROUND OF THE INVENTION

Balloon angioplasty, atherectomy, and stent implantation are common procedures for the treatment of stenotic or diseased lumens. Such procedures are performed percutaneously, through an incision site remote from the site of treatment within the lumen. These procedures consequently require tracking of the treatment device from the incision site, through the vasculature and to the lesion. The vasculature is typically tortuous and may have numerous stenoses of varying degrees throughout its length. In order to place the distal end of a catheter at the treatment site, a guidewire is first tracked from the incision, through the stenosis, and across the lesion. Then, a catheter bearing a balloon and/or other device such as, for example, a stent, at its distal end can be tracked over the guidewire to the treatment site. Ordinarily, the distal end of the guidewire is quite flexible in order that, as it is pushed through the lumen, it can "find" its way through the turns of the typically irregular passageway of the lumen without damaging the lumen.

In some instances, the extent of occlusion of the lumen is so severe that the lumen is nearly completely obstructed, leaving virtually no passageway for the guidewire. Such a condition may be described as a "total occlusion". Where such a condition persists longer than six months, the lesion is referred to a "chronic total occlusion". Further, in the case of diseased blood vessels, the lining of the vessels may be characterized by the prevalence of atheromatous plaques, which may form a total occlusion. The extensive plaque formation of a chronic total occlusion typically has a fibrous cap surrounding softer plaque material. Such a fibrous cap may present a surface which may be difficult to penetrate with a conventional guidewire. In such instances, the typically flexible distal tip of the guidewire may be unable to cross the lesion, and in order to successfully cross and treat a chronic total occlusion, alternative devices may be required. For example, at a minimum, a stiffer guidewire may be required to traverse the stenosis. Or, an atherectomy device may be required to penetrate the occlusion. Hereinafter, Applicants refer to any device intended to penetrate the occlusion, including a guidewire, as a recanalizing device.

In the event that a recanalizing device and/or greater force by the clinician are required in order to create a passageway through a chronic total occlusion, additional precautions must be taken to prevent injury to the vessel wall. For example, it is imperative that the guidewire and/or atherectomy device be centered within the vessel to avoid penetration of the vessel wall. Further, visualization of the location of the guidewire or atherectomy device exit port is desirable. Therefore, the device and method for centering the recanalizing device within the vessel must confer a high degree of confidence on the clinician, both in centering and in visualization, in order that a passageway can be safely created.

Additionally, in the instance where a stiffer guidewire or other device is required in order to cross the lesion, the guidewire will meet increased resistance upon attempts to penetrate the plaque. Consequently, the guidewire or other device will require increased support proximal of the lesion. That is, when the tip of the guidewire abuts the plaque, and as pressure is exerted upon the guidewire in order to penetrate the lesion, portions of the guidewire proximal of the tip will require the support of a catheter encasing the guidewire. Such "back support" will prevent excessive prolapse of the guidewire or other device within the vessel proximal of the stenosis and will ensure that the recanalizing device remains centered within the lumen.

Further, when the tip of the guidewire or recanalizing device meets increased resistance to penetration of the lesion, an additional result may be a tendency of the catheter to slide proximally over the guidewire. Such proximal sliding will result both in a failure to maintain the recanalizing device centered within the vessel and in a failure to provide back support to the device. Such a tendency may be recurring with repeated attempts to traverse the stenosis, rendering the process increasingly frustrating for the clinician. Means for securing the catheter within the vessel may be required during attempts to penetrate an extensive lesion.

Angioplasty catheters and stent delivery catheters of the prior art lack means for adequate visualization, centering, support and securement of the catheter for treatment of extensive lesions. Similarly, devices bearing cutting heads or other devices for creating a guide wire passage lack means for sufficiently centering the device prior to penetrating the occlusion. Therefore, the prior art devices lack sufficient safeguards and back support for using a stiffer guidewire and lack the essential safeguards for centering a cutting device intended to penetrate an extensive occlusion.

SUMMARY OF THE INVENTION

The present invention provides an apparatus for improved centering of a device which is intended to penetrate a severe occlusion of a body lumen. Further, a device according to the present invention allows for better fluoroscopic visualization, and therefore placement, of the device with respect to the lesion. A device according to the present invention also provides back support for a recanalizing device during attempts to penetrate an extensive occlusion. Still further, a device according to the present invention provides a friction fit of the device with the vessel wall during attempts to cross a lesion, preventing proximal sliding of the device during attempts to cross the lesion. According to the present invention, a catheter with a substantially central lumen for receiving a guidewire and/or other recanalizing device is provided. Further, the central lumen of a catheter according to the invention comprises an exit port which is not distal to the inflatable member of the catheter. An alternative embodiment of the invention also comprises a central lumen for receiving a second catheter for the purpose of conducting an angioplasty procedure and/or delivering a stent. Further, a method of making an inflatable member for use in an apparatus according to the invention is provided.

BRIEF DESCRIPTION OF THE DRAWINGS

FIGS. 4–8 illustrate an embodiment of the invention in use.

FIG. 9 illustrates a cut-away view of a prior art catheter in use at a bifurcation in a vessel.

FIG. 10 illustrates a cut-away view of an embodiment of the invention in use at a bifurcation in a vessel.

DETAILED DESCRIPTION OF THE INVENTION

Figure 1:
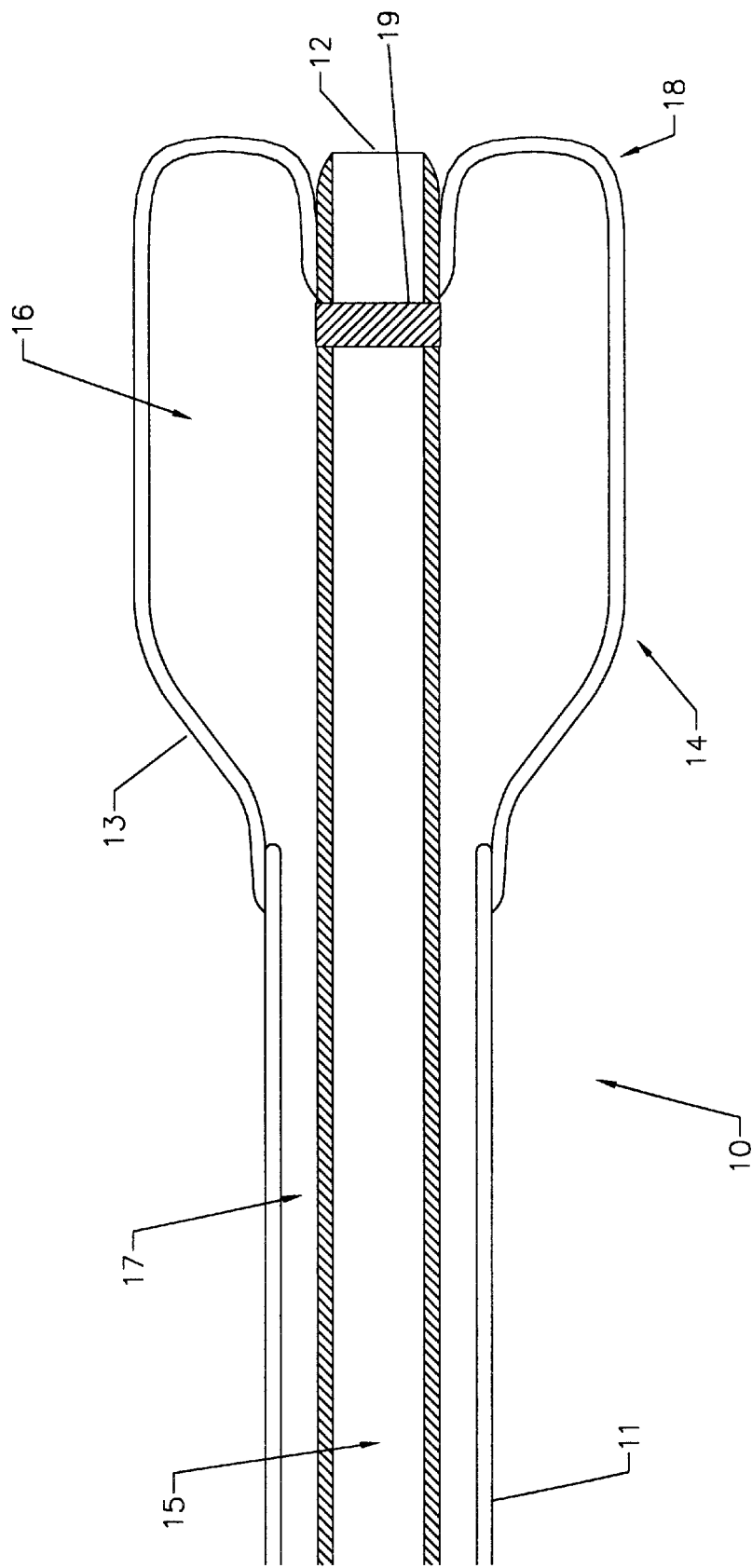
FIG. 1 illustrates a cut-away view of a first embodiment of the invention.

Referring to FIG. 1, a first embodiment of the invention comprises catheter 10 having lumen 15 with exit port 12. Catheter 10 further comprises distal end 14, which includes marker band 19, and balloon 16 in communication with inflation lumen 17. Distal portion 18 of balloon 16 is substantially contiguous with exit port 12. Distal portion 18 and exit port 12 thereby define the distal-most elements of distal end 14 of catheter 10. Balloon 16 is typically but is not of necessity a low-pressure balloon. Balloon 16 is affixed to the exterior surface of tubular member 11 near proximal region 13 of balloon 16 and at some point proximal of exit port 12.

Figure 2:
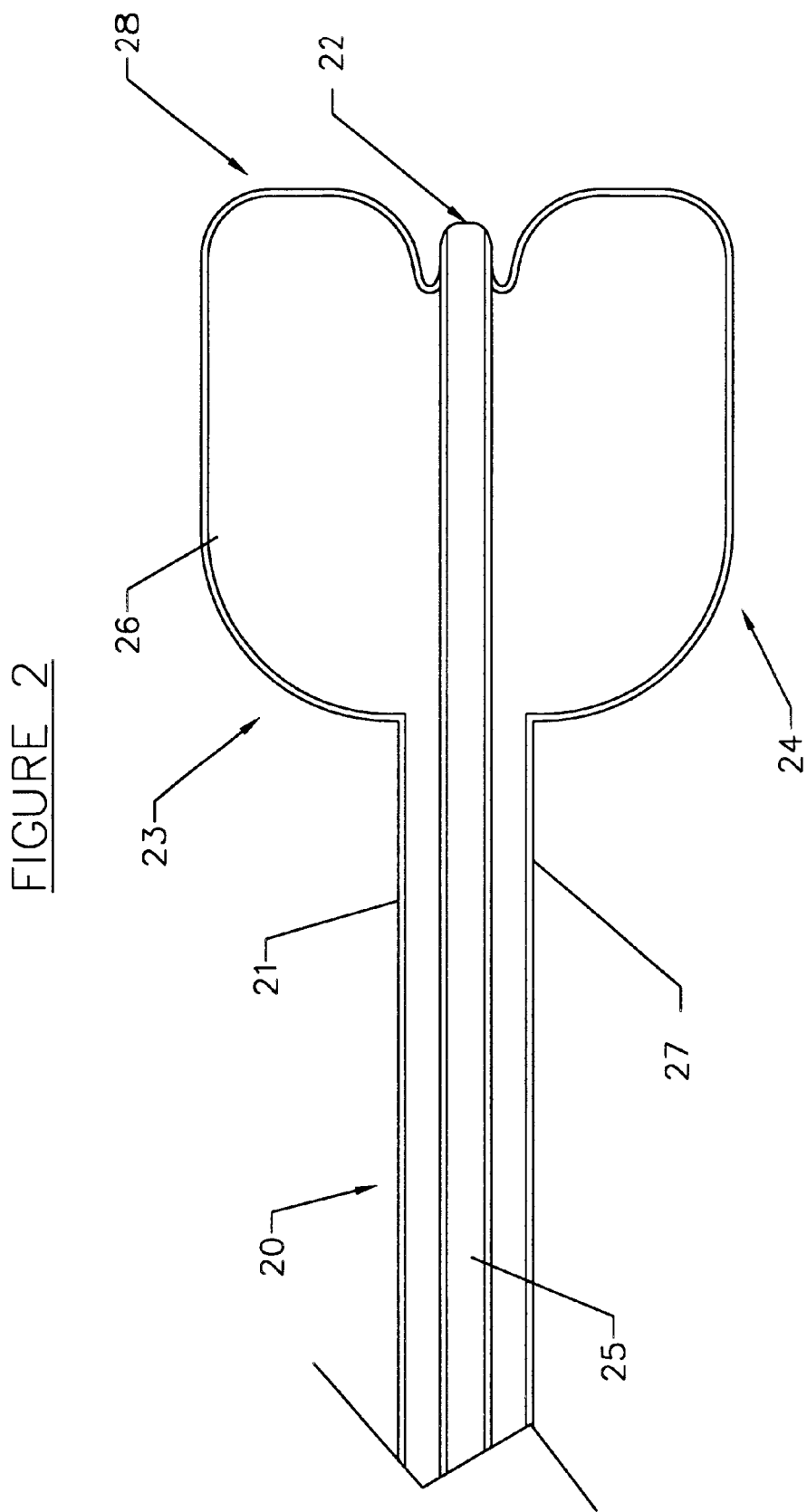
FIG. 2 illustrates a cut-away view of a second embodiment of the invention.

Turning now to FIG. 2, an alternative embodiment of the invention comprises catheter 20 having lumen 25 with exit port 22. Distal end 24 of catheter 20 comprises distal portion 28 of balloon 26, which defines the distal-most element of distal end 24. Distal portion 28 of balloon 26 extends slightly distally of exit port 22. Inflation lumen 27 is in fluid communication with balloon 26. Balloon 26 is affixed to the exterior surface of tubular member 21 near proximal region 23 of balloon 26 and at some point proximal of exit port 22.

Figure 3:
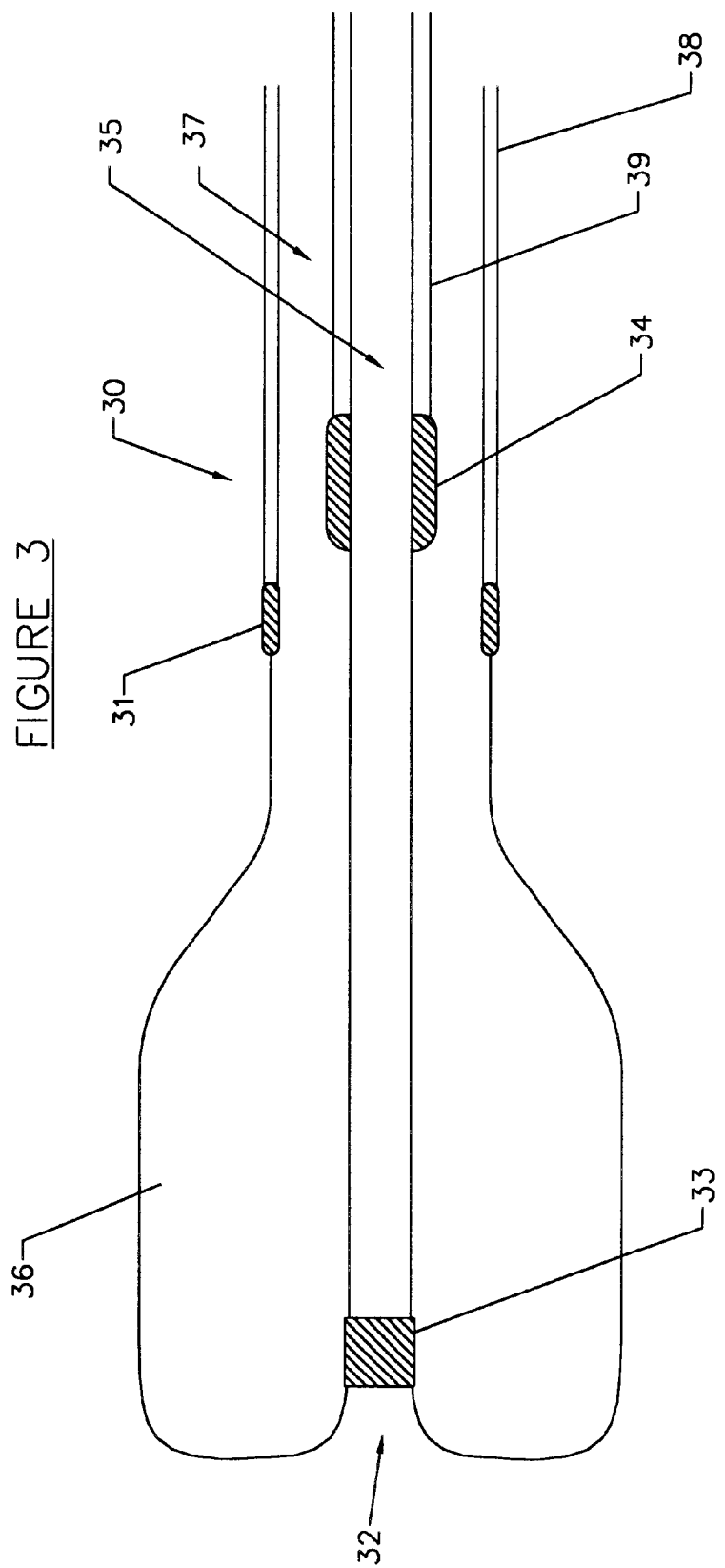
FIG. 3 illustrates a cut-away view of a third embodiment of the invention.

FIG. 3 represents yet another embodiment of the invention. Catheter 30 comprises balloon 36 in fluid communication with inflation lumen 37. Catheter 30 further comprises lumen 35, guidewire exit port 32, and marker band 33. In the embodiment of FIG. 3, marker band 33 is substantially contiguous with exit port 32, allowing for fluoroscopic visualization of the device at its distal-most region. Inner member 39 is bonded to balloon 36 at seal 34. Balloon 36 outer member 38 is bonded to balloon 36 at bond site 31. Laser bonding, thermal bonding, the use of adhesives, or other procedure known in the art can be used to form seal 34 and/or bond site 31.

FIGS. 4–8 demonstrate the advantages of the invention in use within vessel 3. In FIG. 4, standard guidewire 5 is advanced through vessel 1 via guide catheter 6, to the site of chronic total occlusion 2. Used alone, as depicted in FIG. 4, guidewire 5 will not pass chronic total occlusion 2, and will prolapse into the vessel when pressure is applied.

FIG. 5 illustrates prior art catheter 50 comprising prior art balloon 60, and the resulting limitations encountered when attempting to center a device such as a guidewire at the site of chronic total occlusion 2. As illustrated in FIG. 5, guidewire 5 is not directed toward the center of chronic total occlusion 2, and in fact is directed undesirably toward the wall of vessel 3. Using prior art catheter 50, it will be difficult to traverse chronic total occlusion 2 and the risk of perforation of the vessel wall is quite high. And catheter 50 confers no advantage upon the procedure of centering a device such as guidewire 5. However, it will be possible to traverse such a lesion using the instant invention.

Figure 8:
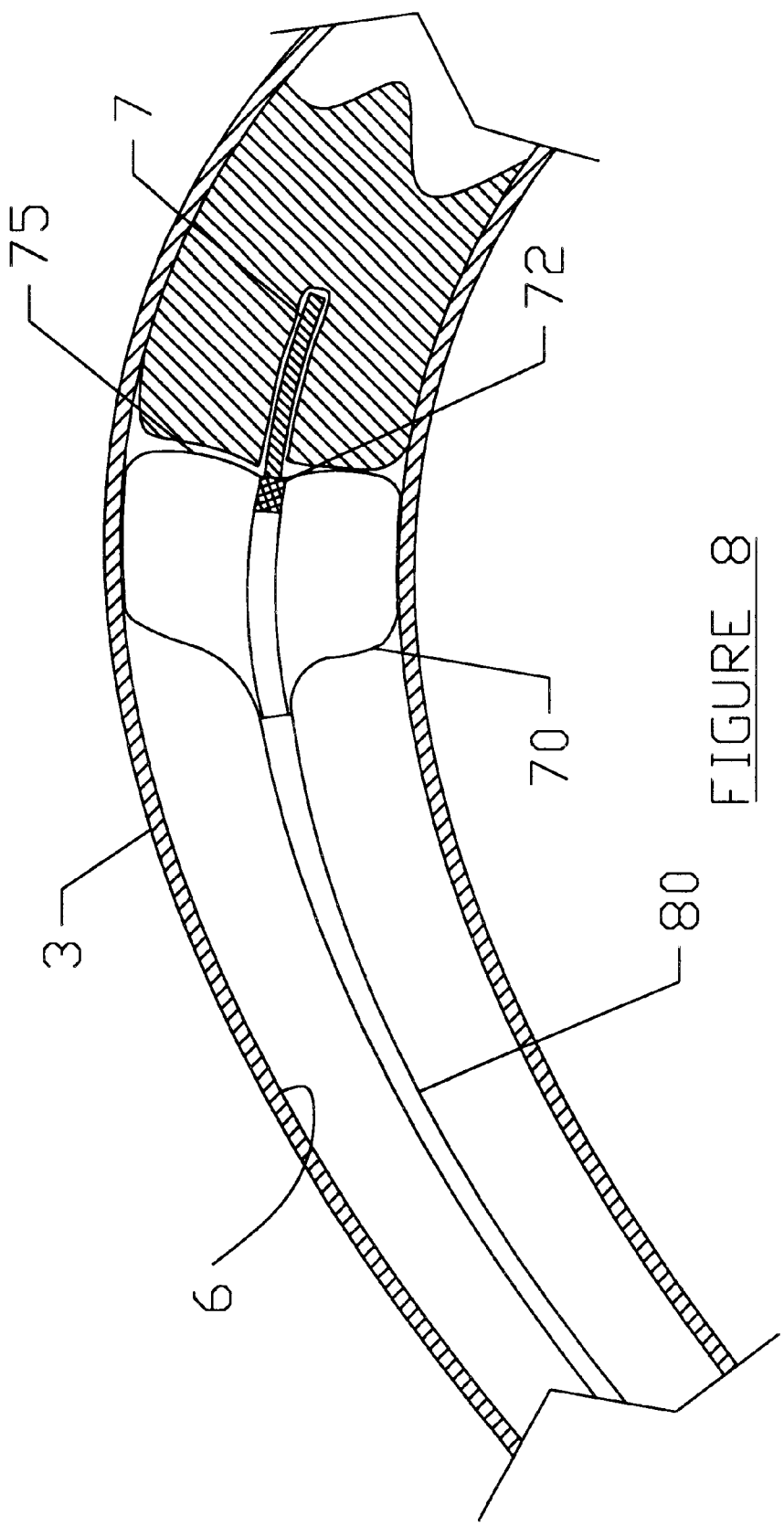

FIGS. 7–8 illustrate the clinical advantages of the invention set forth herein. According to the invention, catheter 80, comprising balloon 70, is advanced over guidewire 5, to the site of chronic total occlusion 2. Because standard guidewire 5 cannot traverse the stenosis, guidewire 5 is withdrawn and replaced by stiffer guidewire 7. Alternatively, a cutting tool, such as an atherectomy device, can be tracked to chronic total occlusion 2. As illustrated in FIG. 8, balloon 70 is then inflated at nominal pressure. When inflated, balloon 70 centers exit port 72, thereby centering stiffer guidewire 7, within the vessel. Distal portion 75 abuts at least a portion of chronic total occlusion 2. Further, according to the embodiment of FIG. 8, catheter 80 also comprises marker band 72 at its distal-most portion. Therefore, marker band 72 also abuts chronic total occlusion 2, and enables the clinician to predict the location of the central region of chronic total occlusion 2. Such improved visualization of the device both at the lesion and at the port where the guidewire emerges from the device confers great advantage on the device over the prior art. Subsequently, stiffer guidewire 7 may be replaced by an alternative tool also designed to penetrate chronic total occlusion 2, or to for example, perform a balloon angioplasty and/or stent delivery procedure. Any such device will also be centered within the vessel via balloon 75 and exit port 72.

Catheter 80 additionally provides support to guidewire 7 within the vessel. As a result, the force exerted upon guidewire 7 to penetrate the lesion is enhanced. And, additional force can be applied to stiffer guidewire 7 without resulting in excessive prolapse of the guidewire within vessel 3. Therefore, it is more likely that guidewire 7 will effectively penetrate chronic total occlusion 2.

Further, after inflation, balloon 70 forms a friction fit with interior wall 6 of vessel 3. Catheter 80 is thereby securely positioned within vessel 3. Therefore, pressure exerted to advance stiffer guidewire 7 or other tool to traverse chronic total occlusion 2 will not deflect catheter 80, or cause catheter 80 to slide proximally within vessel 3. Stable support and consistent centering in conjunction with improved visualization are thereby provided by catheter 80 according to the invention.

Turning now to FIGS. 9 and 10, further advantages of the invention are described. FIG. 9 illustrates the use of a prior art catheter at the site of a bifurcation in a vessel. Prior art catheter 405 has been tracked over guidewire 415 and is shown within vessel 400. Vessel 400 comprises occlusion 410 within first branch 411. Guidewire 415, having encountered occlusion 410, has prolapsed into second branch 420. And, prior art catheter 405 is not designed to provide support to or enable guidewire 415, or an alternate device (not pictured) to traverse the lesion. Consequently, it will be difficult, if not impossible, to traverse occlusion 410 utilizing only the prior art devices.

In FIG. 10, catheter 505 according to the invention has been tracked over a conventional guidewire (not shown) to occlusion 510 within first branch 511 of bifurcated vessel 500. Balloon 506 of catheter 505 centers and supports stiffer guidewire 515 in order that guidewire 515 can traverse occlusion 510. Further, balloon 506 prevents prolapse of guidewire 515 into second branch 520.

FIGS. 11–14 illustrate successive steps of preparing a balloon for use in a device according to the invention. First, as shown in FIG. 9, balloon 110 comprises central portion 111, distal shaft 100 and proximal shaft 115. Distal shaft 100 comprises exterior surface 101, and proximal shaft 115 comprises interior surface 102 and exterior surface 103.

Figure 11:
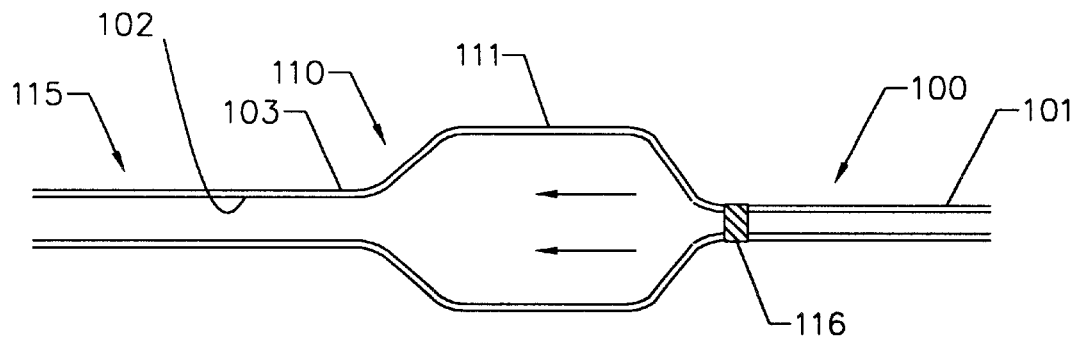
FIGS. 11–14 illustrate successive steps of one method of manufacturing a balloon for use in a device according to the present invention.
Figure 12:
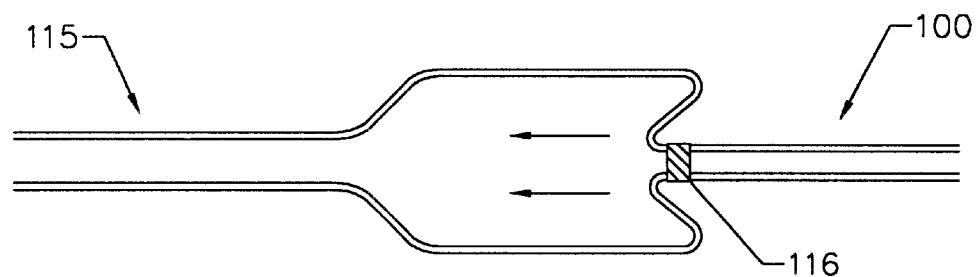
Figure 13:
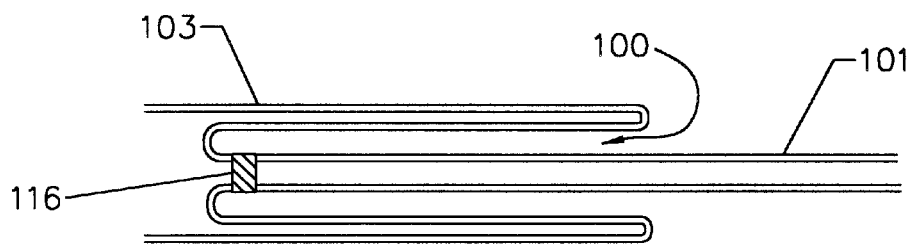
Figure 14:
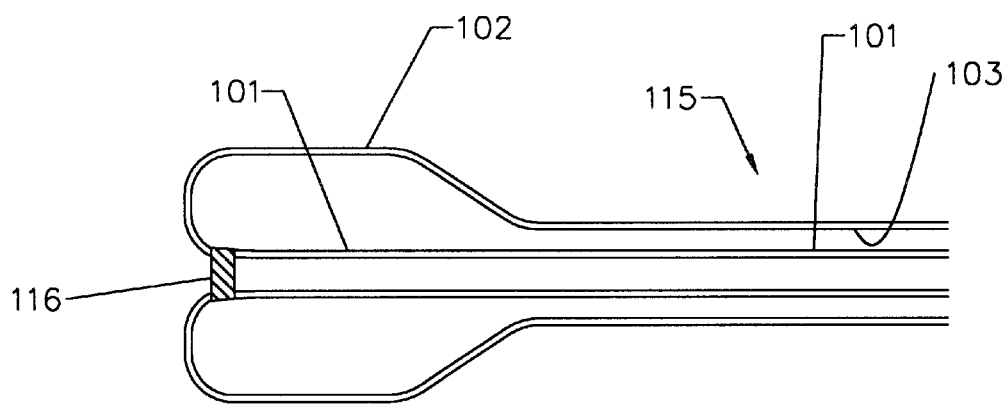

Distal shaft 100 further comprises marker band 116. Alternatively, marker band 116 can be placed on the catheter as a later step in the manufacturing process. In either case, according to the invention, marker band 116 can be placed at substantially the distal-most portion of balloon 110, conferring great advantage over the prior art for visualizing the device at the site of total occlusion. As shown in FIG. 10, distal shaft 100 is withdrawn into balloon 110, until distal shaft 100 is within central portion 111 of balloon 110, as shown in FIG. 11. Proximal shaft 115 is then inverted until interior surface 102 is exposed, and exterior surface 103 is adjacent exterior surface 101. FIG. 12 illustrates the configuration of balloon 110 after proximal shaft 115 is completely inverted over distal shaft 100 of balloon 110. Balloon 110 is now ready to be affixed to a catheter member (not pictured) using any process known in the art.

Figure 15:
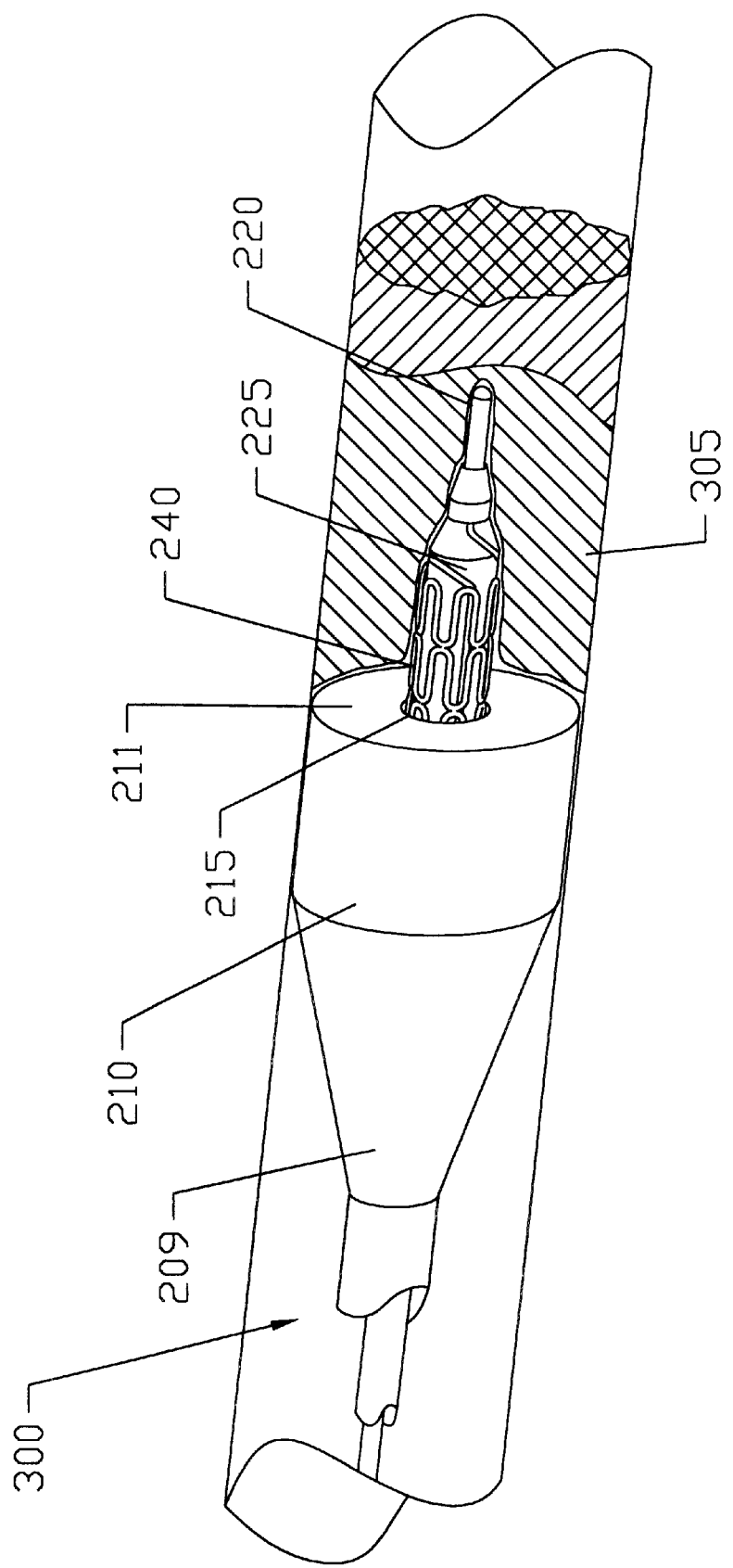
FIG. 15 illustrates a side view of an alternative embodiment of the invention.

Turning now to FIG. 15, an alternative embodiment of the invention is shown within vessel 300 at the site of chronic total occlusion 305. The embodiment depicted in FIG. 13 comprises catheter 209 having balloon 210. Distal portion 211 of balloon 210 is the distal most element of catheter 209. Balloon 210 also comprises central lumen 215. Once catheter 209 is positioned within vessel 300, balloon 210 is inflated to abut chronic total occlusion 305. Next, second catheter 225 can be tracked over guidewire 220, through central lumen 215. Second catheter 225 can be a more conventional balloon catheter and/or a catheter designed for stent delivery and deployment. In the embodiment depicted in FIG. 13, stent 240 can be delivered to the site of chronic total occlusion 305.

A balloon catheter assembly and method of manufacturing a balloon catheter assembly have been disclosed. Although the present invention has been described in accordance with the embodiments shown, one of ordinary skill in the art will readily recognize that there could be variations to the embodiments and those variations would be within the spirit and scope of the present invention.

A wide variety of suitable materials used for balloons and tubular members may be interchanged without diverging from the methods or structures of the invention claimed. Further, the guide wire or atherectomy device type utilized could be varied greatly. The embodiments disclosed herein focus on conventional guidewires, catheters, balloons and stents comprising conventional materials, but alternative structures and materials may also be used.

Further, the instant invention can also be used for treatment of conditions other than chronic total occlusions. Other examples of therapies include mitral valvuloplasty, treatment of urethral blockages and blockage of the fallopian tubes. The foregoing embodiments and examples are illustrative and are in no way intended to limit the scope of the claims set forth herein.

We claim:

1. A device for treating an occluded body lumen, said device comprising a proximal end and a distal end;

a substantially tubular member comprising an exit port; and an inflatable member having a distal end;

wherein the exit port is not distal to the inflatable member.

2. The device according to claim 1, wherein said inflatable member further comprises a proximal portion and a distal portion, and wherein the exit port is substantially contiguous with the distal portion of the inflatable member.

3. The device according to claim 1, wherein said inflatable member further comprises a proximal portion and a distal portion, and the exit port is proximal to the distal end of the inflatable member.

4. An apparatus for centering a recanalizing device within a body lumen comprising a proximal end and a distal end;

a substantially tubular member comprising an exit port; and an inflatable member having a distal end;

wherein the exit port is not distal to the inflatable member.

5. The apparatus according to claim 4, wherein the inflatable member further comprises a proximal portion and a distal portion; and the exit port is substantially contiguous with the distal end of the inflatable member.

6. The apparatus according to claim 4, wherein the inflatable member further comprises a proximal portion and a distal portion; and the exit port is proximal to the distal end of the inflatable member.

7. A method of making an inflatable member for use in a device for treating an occluded lumen, said method comprising the steps of:

providing an inflatable member comprising an interior surface, an exterior surface, a proximal shaft, a middle portion, and a distal shaft;

inverting the exterior surface of the proximal shaft such that the exterior surface of the proximal shaft faces the exterior surface of the distal shaft.

8. A method of making a catheter for treating an occluded lumen, said method comprising the steps of:

providing an inflatable member comprising an interior surface, an exterior surface, a proximal shaft, a middle portion, and a distal shaft;

inverting the exterior surface of the proximal shaft such that the exterior surface of the proximal shaft faces the exterior surface of the distal shaft;

placing a first tubular member over the exterior surface of the distal shaft;

affixing the exterior surface of the distal shaft to the first tubular member;

placing a second tubular member over the exposed interior surface of the proximal shaft; and affixing the exposed interior surface of the proximal shaft to the second tubular member.

* * * * *